United States Patent
Bickley et al.

(10) Patent No.: US 11,612,846 B2
(45) Date of Patent: Mar. 28, 2023

(54) LOW DEAD SPACE LAMINAR FLOW WATER FILTER FOR SIDE STREAM $CO_2$ MONITORING LINES

(71) Applicant: Westmed, Inc., Centennial, CO (US)

(72) Inventors: James Dale Bickley, St. Louis, MO (US); Robert Jon McKinnon, Highlands Ranch, CO (US); Geon Seok Seo, Tucson, AZ (US)

(73) Assignee: WESTMED, INC., Centennial, CO (US)

( * ) Notice: Subject to any disclaimer, the term of this patent is extended or adjusted under 35 U.S.C. 154(b) by 634 days.

(21) Appl. No.: 16/299,526

(22) Filed: Mar. 12, 2019

(65) Prior Publication Data

US 2019/0274589 A1  Sep. 12, 2019

Related U.S. Application Data

(60) Provisional application No. 62/783,469, filed on Dec. 21, 2018, provisional application No. 62/641,548, filed on Mar. 12, 2018.

(51) Int. Cl.
| | |
|---|---|
| *B01D 46/62* | (2022.01) |
| *A61B 5/083* | (2006.01) |
| *A61B 5/097* | (2006.01) |
| *B01D 53/26* | (2006.01) |

(Continued)

(52) U.S. Cl.
CPC ........... *B01D 46/62* (2022.01); *A61B 5/0836* (2013.01); *A61B 5/097* (2013.01); *B01D 39/16* (2013.01); *B01D 46/0036* (2013.01); *B01D 46/0086* (2013.01); *B01D 53/261* (2013.01); *B01D 53/266* (2013.01); *B01D 2267/40* (2013.01)

(58) Field of Classification Search
CPC ......... A61B 5/097; A61B 5/0836; A61B 5/08; A61B 5/085; A61B 5/087; A61B 5/0871; A61B 5/0873; A61B 5/0875; A61B 5/0876; A61B 5/0878; B01D 53/261; B01D 53/266; B01D 39/16; B01D 46/0023; B01D 46/0036; B01D 46/0086; B01D 2267/40; B01D 2239/0421; B01D 2239/0428
See application file for complete search history.

(56) References Cited

U.S. PATENT DOCUMENTS

| | | | |
|---|---|---|---|
| 5,357,971 A | * | 10/1994 | Sheehan ............... G01N 33/497 600/532 |
| 5,657,750 A | | 8/1997 | Colman et al. |
| 6,689,278 B2 | | 2/2004 | Beplate |

(Continued)

OTHER PUBLICATIONS

AEDSuperstore. (2011). Physio-Control LIFEPAK 12 CapnoLine Smart Plus. Accessed May 17, 2021 at https://www.aedsuperstore.com/physio-control-lifepak-12-smart-capnoline-plus-long-o2-adult-intermediate.html (Year: 2011).*

*Primary Examiner* — Jonathan Miller
*Assistant Examiner* — Gabriel E Gitman
(74) *Attorney, Agent, or Firm* — Sheridan Ross P.C.

(57) ABSTRACT

A water filter system for a $CO_2$ sampling line positioned between a patient and a patient monitor to receive patient exhalation. The filter system includes at least one hydrophobic filter that adsorbs and prevents water from reaching the patient monitor. Alternatively, the filter system may include both a hydrophobic filter and a hydrophilic filter and optionally a desiccant.

14 Claims, 6 Drawing Sheets

(51) Int. Cl.
  *B01D 39/16*   (2006.01)
  *B01D 46/00*   (2022.01)

(56) References Cited

U.S. PATENT DOCUMENTS

| | | | |
|---|---|---|---|
| 8,252,080 B2* | 8/2012 | Fudge ................. | A61M 16/085 |
| | | | 55/482 |
| 2003/0216660 A1* | 11/2003 | Ben-Oren .......... | G01N 33/0006 |
| | | | 600/532 |
| 2004/0060443 A1* | 4/2004 | Richardson ............ | A61B 5/097 |
| | | | 96/108 |
| 2012/0318139 A1* | 12/2012 | Mao ................... | B01D 39/1661 |
| | | | 95/116 |
| 2015/0208952 A1* | 7/2015 | Addison ........... | A61M 16/0808 |
| | | | 600/543 |
| 2015/0217077 A1* | 8/2015 | Scampoli .......... | A61M 16/0057 |
| | | | 600/543 |
| 2015/0223728 A1* | 8/2015 | Fudge ................ | A61M 16/021 |
| | | | 600/532 |
| 2015/0238119 A1* | 8/2015 | Colman ................. | A61B 5/097 |
| | | | 29/428 |
| 2016/0346603 A1* | 12/2016 | Halliday ............. | A61M 16/208 |
| 2017/0119649 A1* | 5/2017 | Zaken ...................... | A61K 8/33 |

* cited by examiner

LOW DEAD SPACE LAMINAR FLOW WATER FILTER FOR SIDE STREAM CO₂ MONITORING LINES

CROSS-REFERENCE TO RELATED APPLICATIONS

The present application claims the benefits of and priority, under 35 U.S.C. § 119(e), to U.S. Provisional Application No. 62/641,548 filed Mar. 12, 2018, and U.S. Provisional Application No. 62/783,469 filed Dec. 21, 2018, the entire disclosures of which are incorporated herein by reference for all purposes.

FIELD OF THE INVENTION

The present disclosure relates to a low dead space generally laminar flow liquid filter for side stream $CO_2$ monitors. In one embodiment, the system includes a hydrophobic filter plus optionally one or more hydrophilic filters to control the flow of water that has condensed out of the exhaled breath or from gases provided by a heated humidification system.

BACKGROUND

Monitoring carbon dioxide ($CO_2$) in the exhaled breath of a patient has been done for many years for several purposes. One of the first reasons $CO_2$ monitoring was used was to determine the proper location of an endotracheal tube. These devices used a colorimetric chemical indicator that would change color in the presence of $CO_2$. Fehder U.S. Pat. No. 4,728,499 is an example of this type of detector that is still in wide use today. Other $CO_2$ detector devices, sold under the brand names of $CO_2$ Easy™ and Pedi $CO_2$ Easy™, are manufactured by Westmed, Inc., Tucson, Ariz. These placement confirmation devices are very effective in determining if the endotracheal tube is in the wrong location, however, they have limitations. This includes the fact they are generally used as a go/no go detector to determine the presence of $CO_2$ and they are not very helpful at quantifying the amount of $CO_2$. They also have a relatively short life in actual conditions of just a few minutes and in ideal conditions up to two hours. Without a graphical display of the $CO_2$ wave form these devices are limited in most cases to an immediate determination of the proper location of the endotracheal tube.

The colorimetric detector was followed by electronic main stream $CO_2$ monitors. This type of monitor requires an adapter with lenses be added to the end of the endotracheal tube and then a breathing circuit is connected to the other end of the adapter that connects the patient to a ventilator. A cable from the monitor is fitted over the adapter so that the cable can shine an infrared light source of the appropriate frequency through one of the lenses of the adapter, through the gas inside the adapter and out of the second lens of the adapter on to a photo diode in the cable assembly to allow the monitor to determine how much light has been adsorbed by the $CO_2$ in the gas sample inside the adaptor. This system allows a generally unlimited monitoring time along with the ability to generate a wave form of the $CO_2$ throughout the breath cycle.

This $CO_2$ wave form can be used to determine a wide variety of patient conditions in addition to the proper location of the endotracheal tube placement. Examples of wave forms and their meanings are shown in FIGS. 1-10. This is not an exhaustive list of wave form types but rather a sample to understand the value of a graphically displayed wave form to understand the critical nature of good resolution of the wave form.

In FIG. 1, the $CO_2$ level begins near zero and the patient exhales. As the exhalation begins the $CO_2$ level quickly begins to rise until the gas from the alveoli begins to reach the monitored location. At this point the $CO_2$ level plateau is reached however a slight increase in the final portion of the exhalation cycle is still seen. As the patient begins to inhale the $CO_2$ level quickly drops back to its base line level near zero.

The wave forms shown in FIGS. 2-10 address other situations that can and do occur with a patient as graphically illustrated with the output of a main stream monitor. FIG. 2 illustrates a wave from in which an endotracheal tube initially is being placed in a patient and ultimately is positioned in the correct location. FIG. 3 illustrates a leaking cuff or right mainstream bronchus. FIG. 4 illustrates a wave form for an endotracheal tube that has become dislodged. FIG. 5 illustrates a wave form where a patient is exhibiting shock. FIG. 6 is a wave form that is indicative of emphysema or a pneumothorax. FIG. 7 is a wave form illustrating a patient with asthma. FIG. 8 is a wave form that is illustrative of a patient with poor lung compliance or, alternatively, one that is pregnant or obese. FIG. 9 is a wave form illustrating a mechanical obstruction in the patient airway. FIG. 10 is a wave form illustrative of a large dead space created by the addition of a disk filter to simulate increased dead space.

The main stream monitors work well; however, they also have their limitations and disadvantages. Because the adaptor needs to be placed between the endotracheal tube and the breathing circuit, it adds dead space to the circuit and forces the patient to rebreathe more of their exhaled CO2. With very small neonatal patients or patients with compromised respiratory systems this can create problems. The cable and its associated electronics and adaptor add weight to the end of the endotracheal tube and has been known to cause the tube to be pulled out of position and to cause kinking of the tube. In addition, main stream devices are generally used with intubated patients. Frequently, however, it is also desired to know the CO2 status of a patient that is not intubated.

To resolve the issues with main stream devices, side stream devices were introduced. All of the electronics are located inside of the monitor and a small sample of the gas from the patient is drawn off or diverted from the main stream with a suction system and brought with a gas sampling line to the remote monitor. The monitor has a sampling chamber where the gas is analyzed in much the same manner as was done with the main stream monitor but all remote from the patient. An example of a commercially available side stream device is the Cleo capnograph module, manufactured and sold by Infinium Medical, Inc., Largo, Fla.

The gas sampling line can be a single tube that connects to a port in the breathing circuit or bite block or it can be part of a cannula or other patient interface device. The key point is a tube will draw off a sample to monitor remote from the patient.

Because the gas sample is monitored remotely from the patient it creates several issues that must be understood and/or dealt with. Because a sample of gases is being drawn off that may be monitored by other equipment in an anesthesia machine or ventilator for example, the sample size must be very small. Frequently the gas sampling line (GSL) will have a very small inside diameter. Common GSL diameters include 0.060", 0.050" and 0.038" inside diameters. To handle this small sample size the monitoring chamber must also be very small. Because the monitor is remote (6 to 25 feet from the patient is not uncommon) the data will lag the actual breathing pattern. Generally, 2 to 5 seconds will pass from the time the patient exhales until the monitored assessment of the exhalation is displayed on the monitor.

This distance also creates a problem with water. When the patient exhales, the temperature of the exhaled gas is normally 37 degrees C. and the gas is at 100% relative humidity. As the gas in the sample line moves to the remote monitor location the impact of the cooler room temperature will cause the gas to cool and some condensation can occur within the sampling line. With the very small monitoring chamber of these devices one small drop of water entering the sampling chamber can disable the monitor requiring very expensive and time-consuming repairs. It is critical the GSL does not allow water to pass through it. Accordingly, water filtration systems have been developed to prevent this. An example of one of the most common water filtration systems used is disclosed in U.S. Pat. No. 5,657,750. This system has a series of hydrophobic tubes that are bent in such a way as the middle of the tube faces the incoming flow of gas and the open ends of the tube face the monitor. The end of the filter where the open ends of the tube is located is then sealed so only gas can pass through the system. Water is stored in the filter housing on the outside of the tube until enough water is accumulated that the filter can no longer pass enough gas for the analyzer to work.

This system has several problems. First because the sample line is small as is the sample chamber it is important to have the gas flow move in a generally laminar flow path with as little dead space as possible. For the sake of this discussion, dead space is created when the gas flow path goes from a small internal diameter (ID) (0.038) to a larger ID. As the gas leaves the small ID tube and enters a larger holding area, the gas that enters that holding area may dwell there for a period of time. Also, the gas may mix with gases from subsequent exhalations. For example, if the gas from the sample tube is from the inhalation cycle and near zero CO2, the holding chamber is filled with gas that has no CO2 present. As the rapidly rising CO2 level is sampled the higher CO2 concentration nearing 5% enters the holding chamber and is diluted by the very low concentration of CO2 in the holding chamber. The opposite is true when the chamber is filled with 5% CO2 and the gas from the GSL delivers low concentrations of CO2 when it samples the next inhalation. An example of the resulting wave form from large dead space is shown below in FIG. 10. This degradation of the wave form reduces and may even eliminate its usefulness in determining the condition of the patient.

It is believed that both turbulent flow and dead spots or zones where flow is slowed or stopped are detrimental to accurate gas analysis as different portions of the sample from the patient breath may mix or blend in either or both of these scenarios. It is further believed that the filter shown in FIG. 4 of U.S. Pat. No. 5,657,750, which is incorporated by reference, not only contains a significant amount of dead space but the flow is not linear. That is the gas may enter at many different locations in the filter tubes and the path the gas takes will determine how quickly it gets through the filter. Gas that enters the filter first may not be the gas that leaves the filter first. Using a filter according to embodiments of the present disclosure forces all of the gas to enter at one end of the filter and all of the gas leaves at the opposite end of the filter with all gas paths being approximately the same creating a more linear path with much less dead space and a higher resolution wave form.

SUMMARY

It is important for optimal patient care to be able to distinguish between and among the wave forms illustrated in FIGS. 1-10 (and other wave forms not illustrated). For example, FIG. 1 shows a normal wave form. The plateau shows the $CO_2$ levels continue to climb slightly until just before it drops on inhalation. In comparison, FIG. 6 shows a similar wave form, but the plateau drops instead of increasing. The FIG. 6 wave form is indicative of a leak in the lung tissue as would be seen with emphysema or a pneumothorax. If healthcare providers cannot distinguish between these two wave forms the treatment for the patient will not be altered in a timely manner which can make the condition worse. A second example is shown by comparing FIGS. 7 and 9. These wave forms are also similar, but one indicates a patient with asthma and the other a patient with an obstruction in their airway. Being able to distinguish between these wave forms requires an expert to observe them but also requires a good quality wave form to examine. The wave forms are commonly monitored by an anesthesiologist nurse or respiratory therapist. The amount of training and experience they have will determine how will they can read the wave forms, but they must have a good quality waveform. Embodiments of the filter system of the present disclosure do not degrade wave forms but it is believed enhance wave forms.

In one embodiment, starting at the monitoring end of the device a connector housing is provided that will connect to the monitor and provide fluid communication between the monitor and the gas sampling line. Preferably this housing will be translucent or clear to allow visual confirmation the filtration system is assembled with a low dead space configuration. A flexible tube is bonded inside the connector. The tube has an inside diameter that will allow the filtration system to be inserted but will provide a seal around the outside diameter of the filter or filters comprising the filtration system. A hydrophobic filter is designed that can be inserted into the tube and is pressed into position leaving a minimum amount of dead space between the filter and the connection to the monitor input. Preferably, the hydrophilic and hydrophobic filters abut, effectively leaving no dead space. Taking manufacturing tolerances into account, for example, rough or uneven end surfaces on the filters, for the embodiments of FIGS. 11 and 13-16 the dead space may be as small as or less than 0.001 cubic inches although advantages are still achieved with larger gaps. The preferable design of this hydrophobic filter is a porous plastic with carboxymethyl cellulose (CMC) added as a sealant against water. This allows for larger pores to allow for good gas flow through the filter but when water enters the filter the CMC will swell up closing the pores and blocking the water and the gas from passing.

Examples of porous plastic materials for use as either a hydrophobic or hydrophilic filter include but are not limited to polyethylene, polypropylene, and nylon. More preferably, examples include ultra-high molecular weight polyethylene (UHMWPE), high-density polyethylene (HDPE), polypropylene (PP), polytetrafluoroethylene (PTFE), and polyvinylidene fluoride (PVDF).

In one embodiment the gas sampling line is adapted to fit the inside diameter of the tube and is bonded in place where one end of the GSL is in contact with the end of the hydrophobic filter leaving no dead space.

In another embodiment, the gas sampling line includes a hydrophilic filter and a hydrophobic filter arranged in abutting relation or near abutting relation and positioned proximate the patient monitor leaving a minimum amount of space between the dual filters and the monitor. Here, the hydrophobic filter is positioned closest to the monitor and the hydrophilic filter is positioned upstream of the hydrophobic filter (closer to the patient end of the sampling line). Thus, if the proximal end of the sampling line or tube is closest to the patient and the distal end is closest to the monitor, the filter system comprising the dual filters is positioned at the distal end of the sampling line. The hydrophobic and hydrophilic filters are sized and designed to be press fit into the tube that comprises the sampling line. The design of the hydrophobic and hydrophilic filters is preferably as described in the preceding paragraphs. A filter system having both a hydrophilic filter and a hydrophobic filter will have a longer life than a filter system having a hydrophobic filter alone. In the dual filter system, water will be first adsorbed by the hydrophilic filter and, only after the hydrophilic filter is saturated will water be received by the hydrophobic filter. Overall, the dual filter system will handle a larger volume of water before the hydrophobic filter is saturated and closes the tube to prevent passage of gas samples.

In another embodiment, the dual filter system may be manufactured as a single filter. In other words, the hydrophilic and hydrophobic filter material may be manufactured as a single filter. The distinct materials comprising the hydrophobic and hydrophilic filters will bond at their interface but will not mix together during the manufacturing process.

In another embodiment according to aspects of the present disclosure, the filter system may include two hydrophilic filters and one hydrophobic filter. Here, one hydrophobic filter and the hydrophilic filter are positioned adjacent each other and proximate the monitor as in the prior embodiments. The second hydrophilic filter is positioned upstream of the dual filters with a short section of sampling line or tubing between the two hydrophilic filters. The position of the second hydrophilic filter relative to the first hydrophilic filter makes little difference. In other words, the two hydrophilic filters may be spaced apart or located proximate to each other. As long as both hydrophilic filters are upstream of the hydrophobic filter, they will both adsorb moisture until then cannot adsorb more and the moisture will pass to the hydrophobic filter.

In yet another embodiment, a desiccant is added to the proximal end of the sampling line (closest to the patient). The desiccant functions to remove moisture from the exhalation of the patient before the moisture has time to condense on the inside wall of the sampling line. In one embodiment, the desiccant is added in the form of a tube added to the sampling line with an open center or core. Moisture in the form of a gas passes through the wall of the desiccant tube and vents to atmosphere. This reduces the relative humidity of the remaining gas in the sampling line and reduces the moisture to be adsorbed by the downstream hydrophilic and hydrophobic filters. Inclusion of the desiccant further increases the life of the filter system.

These and other advantages will be apparent from the embodiments of the present disclosure. The above-described embodiments, objectives, and configurations are neither complete nor exhaustive. As will be appreciated, other embodiments of the present disclosure are possible using, alone or in combination, one or more of the features set forth above or described in detail below. Further, this summary is neither intended nor should it be construed as being representative of the full extent and scope of the present disclosure. The present disclosure sets forth in various levels of detail in the summary, as well as, in the attached drawings and the detailed description embodiments that fall within the scope of the disclosure. Additional aspects of the present disclosure will become more readily apparent from the detailed description, particularly when taken together with the drawings. Moreover, reference made herein to "the present disclosure" or aspects thereof should be understood to mean certain embodiments of the present disclosure and should not necessarily be construed as limiting all embodiments to a particular description.

DESCRIPTION OF THE DRAWINGS

The accompanying drawings, which are incorporated in and constitute a part of the specification, illustrate embodiments of the invention and together with the general description of the invention given above and the detailed description of the drawings given below, serve to explain the principles of these inventions.

While the following disclosure describes the invention in connection with those embodiments presented, one should understand that the invention is not strictly limited to these embodiments. Furthermore, one should understand that the drawings are not necessarily to scale, and that in certain instances, the disclosure may not include details which are not necessary for an understanding of the present invention, such as conventional details of fabrication and assembly.

DETAILED DESCRIPTION

Embodiments of the present disclosure overcome the above described limitations and provide an improved water filtering system and method of removing water from side stream gas sampling lines.

Figure 1:
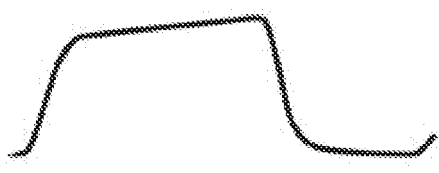
FIG. 1 is a wave form showing $CO_2$ levels of a person during at least one complete breath cycle.
Figure 2:
FIG. 2 is a wave form showing $CO_2$ levels exhibiting a tube placement correction during at least one complete breath cycle.
Figure 3:
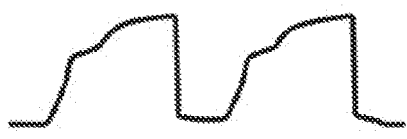
FIG. 3 is a wave form showing $CO_2$ levels exhibiting a leaking cuff or right mainstem bronchus during at least one complete breath cycle.
Figure 4:
FIG. 4 is a wave form showing $CO_2$ levels exhibiting a dislodged tube during at least one complete breath cycle.
Figure 5:
FIG. 5 is a wave form showing $CO_2$ levels exhibiting a shock event, trending down, during at least one complete breath cycle.
Figure 6:
FIG. 6 is a wave form showing $CO_2$ levels exhibiting emphysema or pneumothorax during at least one complete breath cycle.
Figure 7:
FIG. 7 is a wave form showing $CO_2$ levels exhibiting asthma during at least one complete breath cycle.
Figure 8:
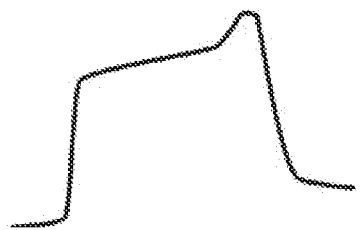
FIG. 8 is a wave form showing $CO_2$ levels exhibiting poor lung compliance or pregnancy or obesity during at least one complete breath cycle.
Figure 9:
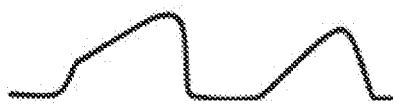
FIG. 9 is a wave form showing $CO_2$ levels exhibiting a mechanical obstruction during at least one complete breath cycle.
Figure 10:
FIG. 10 is a wave form showing $CO_2$ levels exhibiting a large dead space during at least one complete breath cycle.
Figure 11:
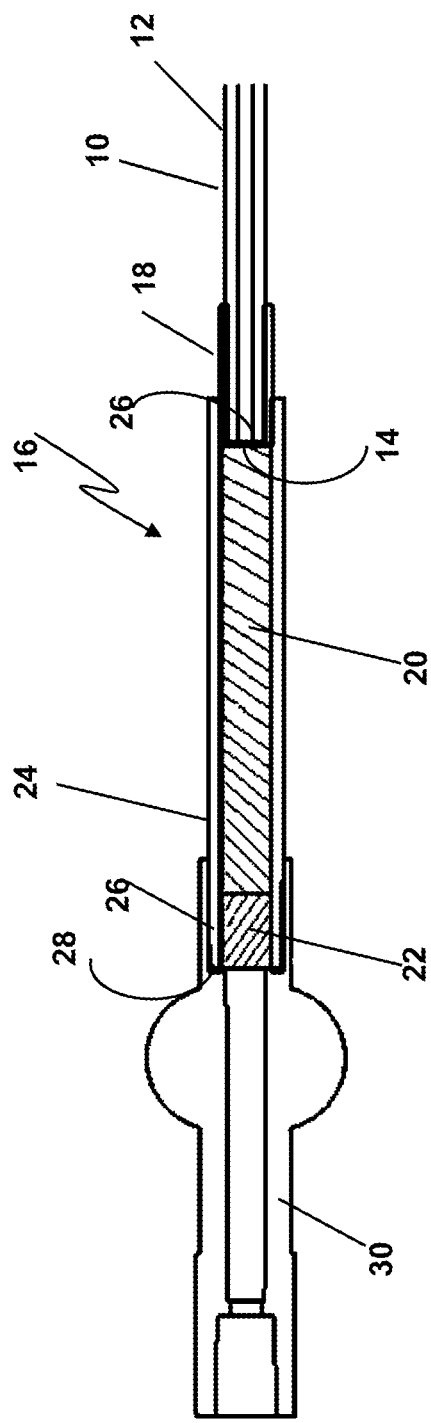
FIG. 11 is a cross section of one embodiment of a gas sampling line according to aspects of the present disclosure.

In one preferred embodiment, for example as shown in FIG. 11, a gas sampling line ("GSL") 10 is provided. One end 12 of the GSL receives exhalation from a patient, and the opposite end 14 would typically connect to and deliver a patient's exhalation to a monitor (not shown). In this embodiment, a filter system 16 is added in-line between the GSL 10 and the monitor. An adapter 18 may be incorporated into and interconnect the GSL 10 to the filter system 16. The filter system 16 includes a hydrophilic filter 20 and a hydrophobic filter 22 both positioned within a tube 24. The two filters are in an abutting relation, leaving no dead space or void between the two filters. The end 14 of the gas sampling line 10 butts up against the end 26 of the hydrophilic filter also leaving no dead space or void. The distal end 28 of the tube 24 communicates with the patient monitor (not shown). A luer connector 30 is illustrated for interconnecting the tube 24 to the monitor, although other connectors may be used as would be known to those of skill in the art. The system has the advantage of allowing the hydrophilic filter 20 to hold water and still pass gas through to the filter containing the water and allowing extended use before becoming saturated. When enough water is accumulated in the hydrophilic filter 20 that it cannot hold more, the water would pass through to the hydrophobic filter 22 and the system is sealed and shut down. In a preferred embodiment, a hydrophilic filter 20 made of porous plastic is used where the pores will, through a capillary effect, collect small amounts of water pulling the water out of the main gas flow pathway. Porous plastic filters of this type may be purchased from Porex Corp., Fairburn, Ga. This system reduces the amount of turbulence in gas flow associated with existing filter systems while removing water and protecting the monitor from damage. Turbulence is undesirable because it can mix discrete and separate gas samples within the sampling line. For example, if the sample in the line is at 0% $CO_2$ and exhalation begins the $CO_2$ level will rapidly increase to approximately 5% $CO_2$. With turbulent flow, the gases will blend some and the 0% will increase earlier than it should, and it will take longer to stabilize at 5% on the wave form. This will result in an altered and inaccurate wave form. Higher levels of $CO_2$ will mix with lower levels of $CO_2$ causing the rounding of the sharp edges of the wave form.

According to aspects of the present disclosure, in one or more preferred embodiments the hydrophobic filter and hydrophilic filter are manufactured as one piece, although they may be separately manufactured and assembled. One example is shown in FIG. 11. This is accomplished by filling a mold with the hydrophobic material to the appropriate depth, then filling the mold the rest of the way with the hydrophilic material. In one embodiment the hydrophobic filter is approximately 0.2 inches deep and approximately 0.13 inches in diameter. The hydrophilic filter is approximately 1.2 inches deep and approximately 0.13 inches in diameter. The volume of each filter may vary and will affect the life of the filter system. The filter material may also vary which can also directly affect the life of the filter system. Examples of hydrophobic and hydrophilic materials includes ultra-high molecular weight polyethylene (UHMWPE), high-density polyethylene (HDPE), polypropylene (PP), polytetrafluoroethylene (PTFE), and polyvinylidene fluoride (PVDF).

The materials will bond to each other but do not mix allowing the hydrophilic material to adsorb water while still allowing gas to flow until the hydrophilic material nears saturation when water would pass to the hydrophobic section sealing the system. This one part would replace both filters shown in the embodiment with one of each filter. That is one end of the filter is made from the hydrophobic material with CMC added and the remainder of the filter is made with hydrophilic material. The filter would be installed with the hydrophobic end facing the machine and the hydrophilic end facing the incoming gas stream. The GSL would butt up against the end of the hydrophilic filter leaving no dead space.

The one possible drawback to the embodiments above is that when the hydrophilic filter is not completely saturated the water contained inside can tend to be drawn in the direction of the gas flow toward the hydrophobic filter. This can result in the hydrophobic filter shutting down the system prior to the hydrophilic filter reaching its maximum saturation point. In bench testing, with a hydrophilic filter section having a 1-inch length and 0.13-inch diameter and an incoming gas flow in the GSL at 37 degrees C. and 100% relative humidity, this occurred in just over 25 hours of continued use. It is believed that increasing the volume of the hydrophilic filter would increase the amount of time before water passes through the filter, for example increasing the length and/or diameter. It is similarly believed decreasing the volume of the hydrophilic filter would decrease the time before water passes through the filter. However, these changes may also alter the shape or quality of the wave form.

Figure 13:
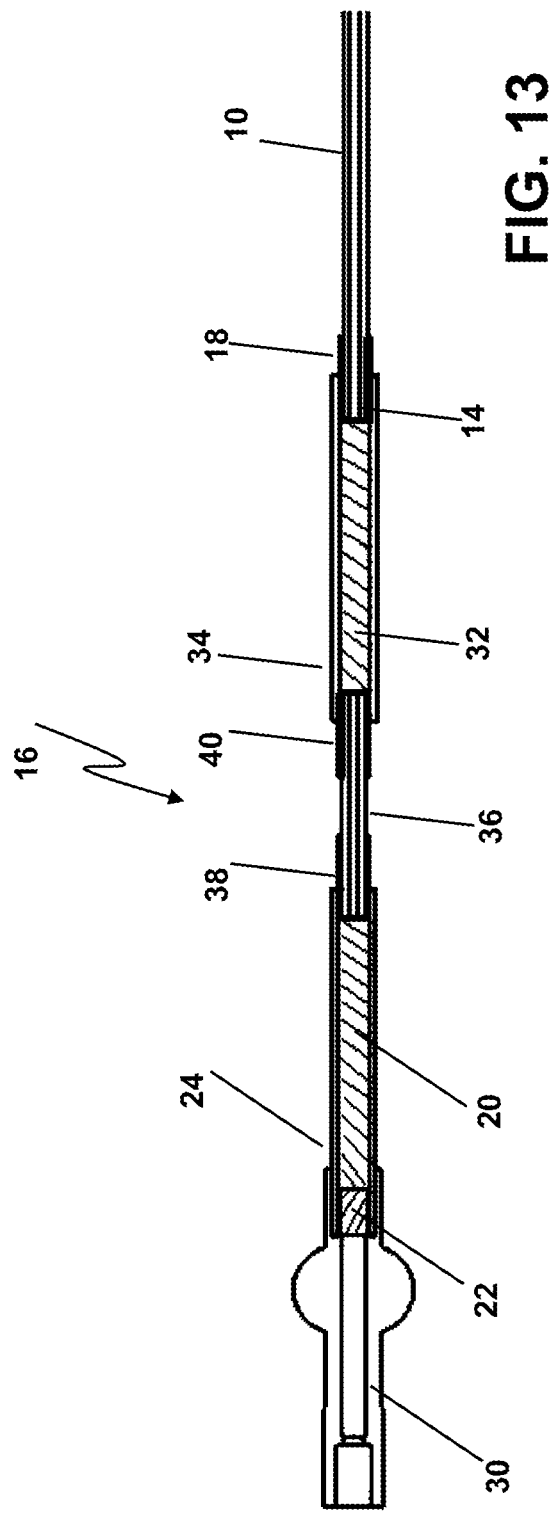
FIG. 13 is a cross section of a second embodiment of a gas sampling line according to aspects of the present disclosure.

In another preferred embodiment according to aspects of the present disclosure, illustrated in FIG. 13, the filter system 16 includes two hydrophilic filters. The second hydrophilic filter 32 is positioned inside tube 34 and is added upstream of the filter system 16 of FIG. 11. A short section of GSL 36 separates the hydrophilic filters 20 and 32. Adapters 38 and 40 interconnect the GSL 36 to the tubes 24 and 34, respectively. Hydrophilic filter 32 abuts the ends of GSL 10 and 36. Hydrophilic filter 20 abuts the GSL 36 and the hydrophobic filter 22. No dead space was added between the hydrophobic filter 22 and the hydrophilic filter 20. This system was tested as before with 37-degree C. gas at 100% relative humidity and the system ran for in excess of 160 hours before passing water through to the hydrophobic filter.

Figure 14:
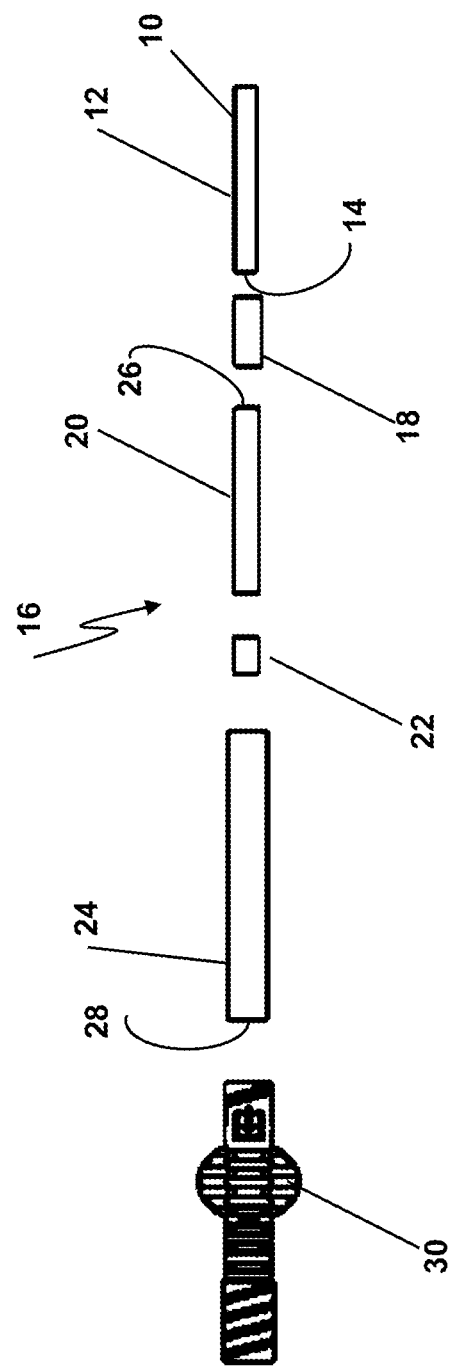
FIG. 14 is an exploded cross section view of a third embodiment of a gas sampling line according to aspects of the present disclosure.
Figure 12:
FIG. 12 is a perspective view of one embodiment of a unitary hydrophobic and hydrophilic filter.

An exploded view of the embodiment of FIG. 11 is shown in FIG. 14. Here, a desiccant is included proximate to the patient end of the tubing to remove moisture from the patient exhalation and thereby prolong the life of the filter system. Because the desiccant is positioned proximate the patient end of the gas line, it is not visible in FIG. 14. In one embodiment, the desiccant is a Nafion tube made by Perma Pure. When air enters the Nafion tube, the molecular humidity (moisture that is still in a gas form) can pass through the walls of the tube and thereby reduce the relative molecular humidity to the same level as that of the ambient air.

For example, in practice a patient exhales gas at 37 degrees C. and 100% relative humidity. As the gas moves through a conventional exhalation tube the gas cools and condensation occurs because the surrounding ambient air is typically cooler. The length of time the gas is in an unheated environment and the cooler the ambient air the faster cooling of the gas occurs, and the more condensation occurs. The condensation will ultimately shut down the system by saturating the hydrophilic filter and then accumulating in the hydrophobic filter. Once the hydrophobic filter is activated, the tubing is blocked, and the filter system must be changed. Adding a desiccant to remove moisture can prolong the life of the system and increase the time between system changes, thereby reducing costs. Adding a Nafion tube into the filter system will drop the humidity to room air and stop or at least reduce condensation.

Set forth below is a table showing 100% and 50% relative humidity at different temperatures. Using this table, a patient exhaling at 100% relative humidity and 37 degrees C. will have 44 milligrams of water in each liter of air. If the same exhalation is passed through a Nafion drier, 50% of the relative humidity will be removed and the moisture content within the exhalation vapor will now be 22 mg/l. Returning to the 100% column, it is shown that 22 mg/l will not cause condensation until the temperature drops to 24 degrees C. Thus, assuming the ambient air is at a temperature greater than 24 degrees C., further condensation will not occur, and the life of the filter system will be extended.

TABLE 1

Relative Humidity

| Temperature (C.) | 100% relative humidity (mg/l) | 50% relative humidity (mg/l) |
| --- | --- | --- |
| 20 | 17 | 9 |
| 21 | 18 | 9 |
| 22 | 19 | 10 |
| 23 | 21 | 11 |
| 24 | 22 | 11 |
| 25 | 23 | 12 |
| 26 | 24 | 12 |
| 27 | 26 | 13 |
| 28 | 27 | 14 |
| 29 | 29 | 15 |
| 30 | 30 | 15 |
| 31 | 32 | 16 |
| 32 | 34 | 17 |
| 33 | 36 | 18 |
| 34 | 38 | 19 |
| 35 | 40 | 20 |
| 36 | 42 | 21 |
| 37 | 44 | 22 |
| 38 | 46 | 23 |
| 39 | 49 | 25 |
| 40 | 51 | 26 |

While the Nafion drier will drop the humidity within the GSL to that of room air and stop condensation, any condensation that occurs prior to the Nafion is still a problem. A Nafion tube will allow gas and water droplets and anything else to flow freely though the inside diameter from one end to the other without restriction. The walls of the Nafion tube prevent gas from leaking from the inside of the tube to atmosphere, however molecular humidity (water vapor) can pass through the walls of the tubing to atmosphere. Water droplets cannot pass through the walls of the tubing and instead pass through the inside diameter from one end of the Nafion tube to the other, so the water is still in the inside lumen of the gas sampling line. Liquid water will remain inside the gas sampling line where it travels to the filter system and may eventually activate and block the hydrophobic filter and shut down the system. To resolve this issue and allow a greater time of use of the filter system before water can shut down the system, embodiments of the present disclosure incorporate a hydrophilic filter in the gas sampling line downstream of or after the drier. The desiccant or drier is located as close as practical to the patient end of the gas sampling line and the hydrophilic filter is located after the drier. Preferably, the hydrophilic filter is approximately 1 inch downstream of the drier, and more preferably the hydrophilic filter is less than one inch from the drier.

Figure 15:
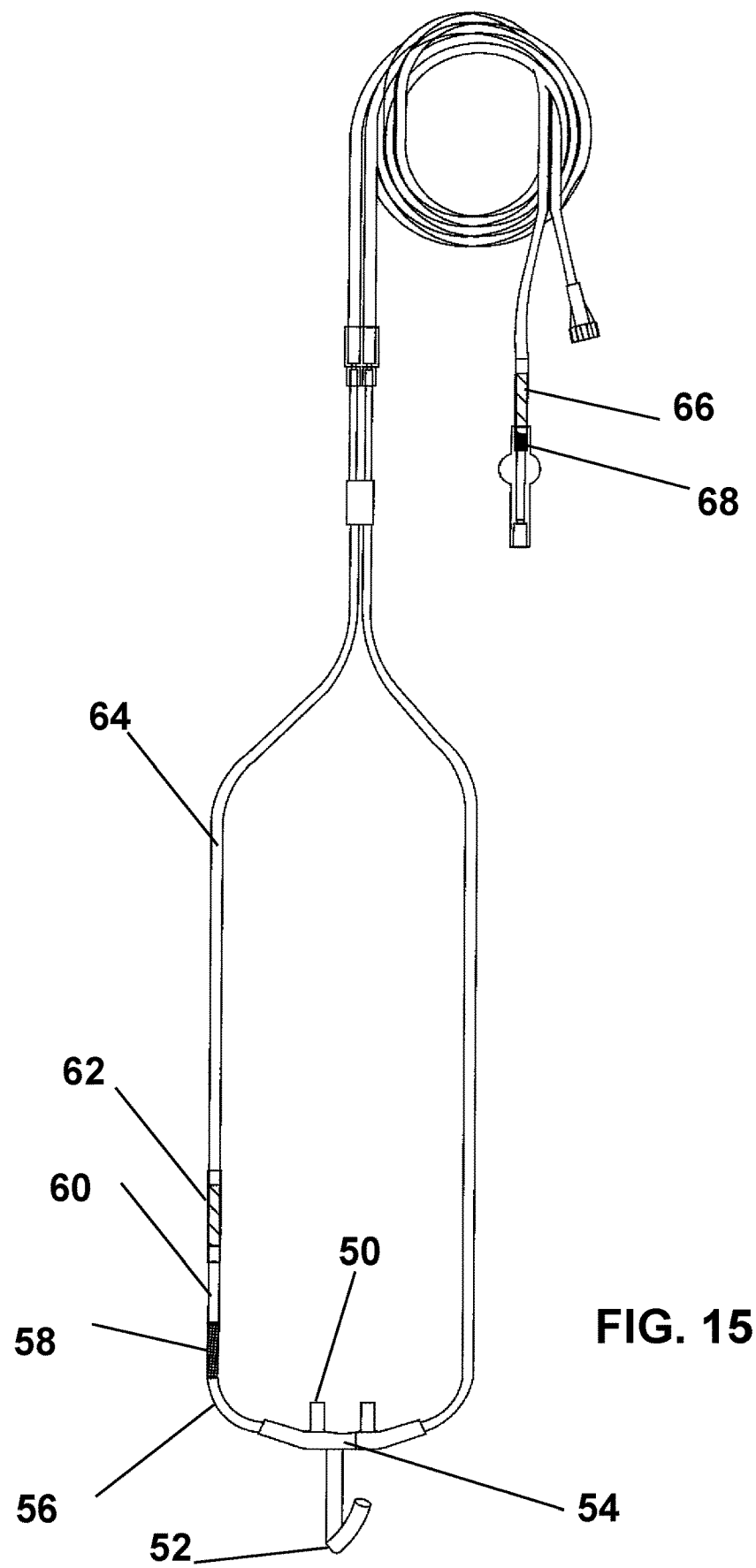
FIG. 15 is a plan view of a fourth embodiment of a gas sampling line incorporating a filtration system according to aspects of the present disclosure, with cross-hatching to better illustrate particular component parts of the filtration system.

FIG. 15 is an illustration of one embodiment of a filter system using a Nafion drier. Gas enters the system in the nasal port 50 or the oral port 52 of the patient nosepiece 54. In one example, the gas is at 100% relative humidity and 37 degrees C. However, the gas will cool quickly in a typical ambient unheated environment. The gas will enter the gas sampling line 56 and then enter the Nafion drier 58. The close proximity of the Nafion drier 58 to the patient port (50 or 52) reduces the amount of condensation that can form in the sampling line 56. As the gas leaves the Nafion drier 58 and enters the next section of gas sampling line 60 the relative humidity of the gas sample will have dropped to 50% in this example. While additional cooling will occur as the sample travels through the rest of the system, the humidity is now sufficiently low that very little condensation, if any, is possible. Any water droplets that form prior to the Nafion drier 58 will be adsorbed by the downstream hydrophilic filter 62 because the condensation will pass through the Nafion drier 58 and the next section of gas sampling line 60 and interface with hydrophilic filter 62. Because the gas that is passing through the hydrophilic filter 62 is now at 50% relative humidity, the water vapor that is still in the gas line has a relative humidity low enough that it will not cause any condensation to occur. As a result, no water will move from the gas in the line into the hydrophilic filter. Significantly more gas now can pass through the hydrophilic filter and the filter will not adsorb any water out of the gas. It only adsorbs the water than has condensed out—not water vapor. Water droplets that form prior to the Nafion drier will get adsorbed and then any droplets of water previously adsorbed by the hydrophilic filter will be evaporated into the drier gas coming out of the Nafion and will pass through the next section of gas sampling line 64 to the second hydrophilic filter 66. The second hydrophilic filter 66 will adsorb additional moisture that may condense in line 64 and until the point of saturation will facilitate such moisture evaporating into the gas traveling through the sampling line. In the event the second hydrophilic filter 66 becomes saturated the hydrophobic filter 68 will adsorb the moisture and shut down the system thereby protecting the monitoring device before the moisture can enter the gas monitor (not shown). As a result, the life of the filter system is further enhanced over filter systems that do not utilize a drier.

Figure 16:
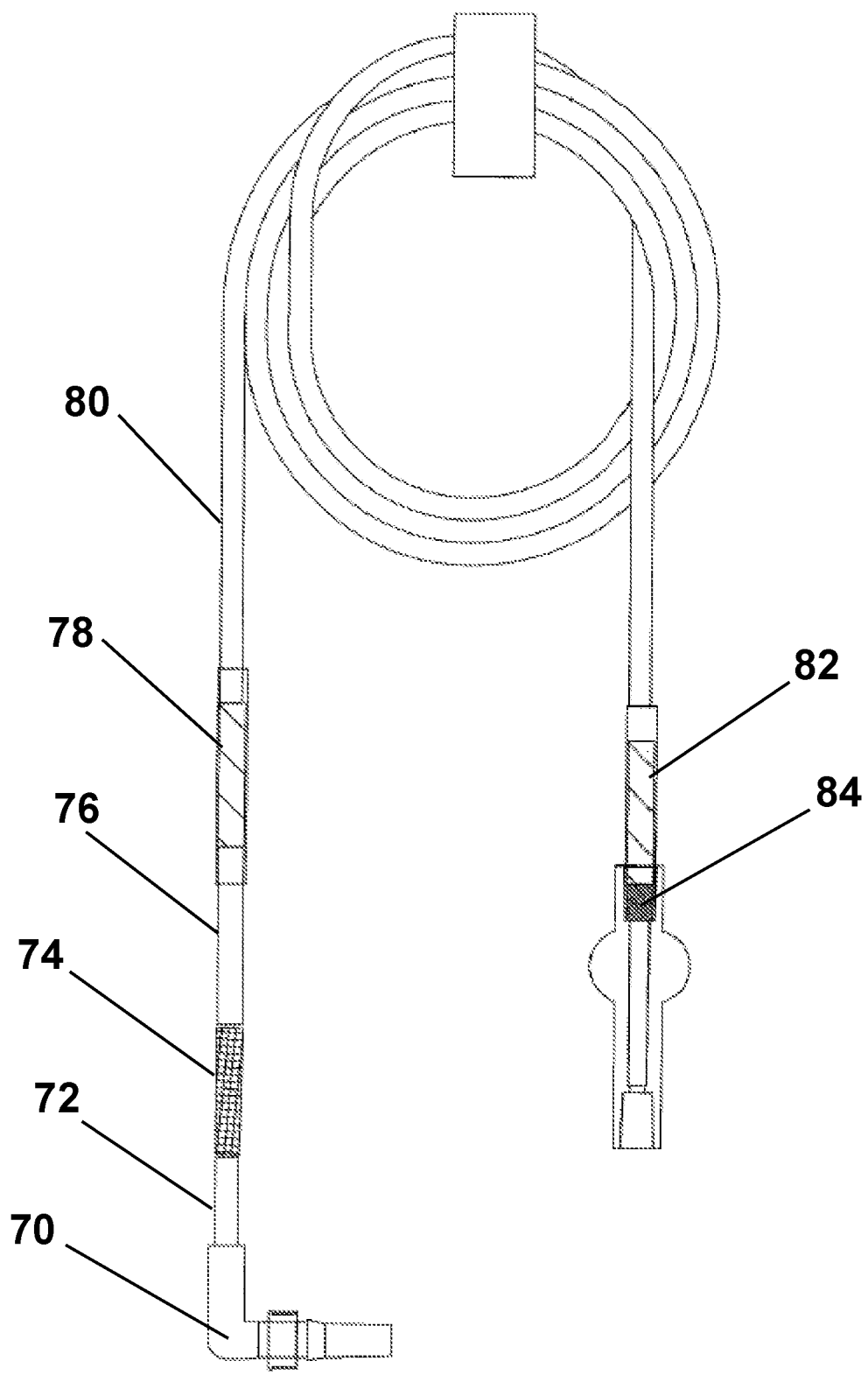
FIG. 16 is a plan view of a fifth embodiment of a gas sampling line incorporating a drying system according to aspects of the present disclosure, with cross-hatching to better illustrate particular component parts of the filtration system.

A further embodiment of a filter system incorporating a drier or desiccant is shown FIG. 16. The standalone gas sampling line shown above works on the same principal. The gas enters the system through a luer connector 70 and again is at 100% relative humidity and 37 degrees C. The gas then passes through a small section of gas sampling line 72 to the Nafion drier 74. When the gas leaves the Nafion drier 74 the relative humidity will have dropped to ambient (50% in this case) as it enters the next section of gas sampling line 76. From the gas sampling line the gas and any droplets of water enter the first hydrophilic filter 78 where the droplets of water are adsorbed and held until the lower relative humidity gas causes the water to evaporate. The gas then enters the remainder of the gas sampling line 80 and travels to the second hydrophilic filter 82 and hydrophobic filter 84 prior to being passed to the gas sampling machine (not shown).

In the foregoing Detailed Description for example, various features of the invention are grouped together in one or more embodiments for the purpose of streamlining the disclosure. This method of disclosure is not to be interpreted as reflecting an intention that the claimed invention requires more features than are expressly recited in each claim. Rather, as the following claims reflect, inventive aspects lie in less than all features of a single foregoing disclosed embodiment. Thus, the following claims are hereby incorporated into this Detailed Description, with each claim standing on its own as a separate preferred embodiment of the invention.

While various embodiments of the safety system present invention have been described in detail, it is apparent that modifications and alterations of those embodiments will occur to those skilled in the art. However, it is to be expressly understood that such modifications and alterations are within the scope and spirit of the present invention. In addition, it should be understood that the drawings are not necessarily to scale. In certain instances, details that are not necessary for an understanding of the invention or that render other details difficult to perceive may have been omitted. It should be understood, of course, that the invention is not necessarily limited to the particular embodiments illustrated herein. Other modifications or uses for the present invention will also occur to those of skill in the art after reading the present disclosure. Such modifications or uses are deemed to be within the scope of the present invention.

The invention claimed is:

1. A water filter system for a side stream $CO_2$ monitor, comprising:
   a. a fluid circuit comprising a gas sampling line having a first section and a second section, each section having a first end and a second end and an internal passage extending between the first end and the second end, wherein the first end of the first section is configured to interconnect to a patient interface, and the fluid circuit is configured to communicate fluid from a patient to a monitoring device;
   b. a first filter system comprising a first hollow tube having a first end and a second end, a first hydrophilic filter disposed within the first hollow tube and having a first end oriented closer to the first end of the first hollow tube and a second end oriented closer to the second end of the first hollow tube, wherein the first end of the first hollow tube is connected to the second end of the first section of the gas sampling line and the second end of the first hollow tube is connected to the first end of the second section of the gas sampling line, and wherein the first hydrophilic filter is sized to adsorb liquid flowing from the first section to the second section;
   c. a second filter system comprising a second hollow tube having a first end and a second end, a second hydrophilic filter having a first end and a second end disposed within the second hollow tube, and a hydrophobic filter having a first end and a second end disposed within the second hollow tube, wherein the first end of the second hydrophilic filter is oriented closer to the first end of the second hollow tube and the second end of the hydrophobic filter is oriented closer to the second end of the second hollow tube and the second end of the second hydrophilic filter abuts the first end of the hydrophobic filter, wherein the second hydrophilic filter is sized to adsorb the flow of liquid in the fluid circuit and the hydrophobic filter is sized to prevent any liquid from reaching the monitoring device, and wherein the second section of the gas sampling line separates the first hydrophilic filter and the second hydrophilic filter; and
   d. a desiccant positioned in the first section of the fluid circuit at a distance of one inch or less from the first hydrophilic filter.

2. The water filter system of claim 1, wherein the hydrophobic filter has properties that seal the fluid circuit when exposed to liquid water but allow water vapor to pass through.

3. The water filter system of claim 2, where said hydrophobic filter is comprised of a porous plastic.

4. The water filter system of claim 3, where the porous plastic contains CMC to seal the pores when exposed to water.

5. The water filter system of claim 1, wherein the fluid circuit is translucent allowing visual confirmation of the positioning of the filter.

6. The water filter system of claim 1, wherein the internal passage of the first section of the gas sampling line has a constant internal diameter and the internal passage of the second section of the gas sampling line has a constant internal diameter, wherein the second end of the second section of gas sampling line abuts the first end of the second hydrophilic filter.

7. The water filter system of claim 6, wherein the first end of the second section of the gas sampling line abuts the second end of the first hydrophilic filter and the second end of the first section of the gas sampling line abuts the first end of the first hydrophilic filter.

8. The water filter system of claim 3, wherein the porous plastic comprises at least one of ultra-high molecular weight polyethylene (UHMWPE), high-density polyethylene (HDPE), polypropylene (PP), polytetrafluoroethylene (PTFE), and polyvinylidene fluoride (PVDF).

9. A water filter system for a side stream $CO_2$ monitor comprising:
   a. a fluid circuit comprising:
      a gas sampling line having at least two sections,
      wherein each section has a first end and a second end, a constant diameter internal passage extends between the first end and the second end, and a respective external diameter, the first end of the first section is configured to interconnect to a patient interface, the second end of the second section is configured to interconnect to a monitoring device, and the fluid circuit is configured to communicate fluid from a patient to the monitoring device;
   b. a first filter system positioned between the first section of the gas sampling line and the second section of the gas sampling line, the first filter system comprising:
      a first tube having an internal diameter equal to or larger than the external diameter of the first section of the gas sampling line and the second section of the gas sampling line, and
      a first hydrophilic filter positioned within the first tube and having a first end and a second end,
      wherein the second end of the first section of the gas sampling line abuts the first end of the first hydrophilic filter and the first end of the second section of the gas sampling line abuts the second end of the first hydrophilic filter such that no dead space is provided in the first filter system;

c. a second filter system disposed within a second tube, the second tube having a first end, a second end, and an internal diameter equal to or larger than the respective external diameters of the first and second sections of the gas sampling line, wherein the second filter system comprises:
 a second hydrophilic filter positioned within the second tube and having a first end and a second end, and
 a hydrophobic filter positioned within the second tube and having a first end and a second end,
 wherein the second end of the second hydrophilic filter abuts the first end of the hydrophobic filter, the second end of the second section of the gas sampling line is positioned adjacent the first end of the second hydrophilic filter such that no dead space is created between the second hydrophilic filter and the second end of the second section of the fluid circuit and such that the second tube is downstream of the first tube, and
 wherein the first filter system and second filter systems are sized to block a flow of liquid in the fluid circuit such that no liquid reaches the monitoring device; and d. a desiccant positioned in the first section of the fluid circuit at a distance of one inch or less from the first hydrophilic filter.

10. The water filter system of claim 9, wherein the hydrophobic filter comprises a porous plastic.

11. The water filter system of claim 9, wherein the first end of the second section of the gas sampling line is positioned inside the second end of the second tube and the second end of the first section of the gas sampling line is positioned inside the first end of the second tube.

12. The water filter system of claim 9, wherein the first and second hydrophilic filters and the hydrophobic filter each have a diameter larger than that of the first tube and are press fit inside the first and second tubes.

13. The water filter system of claim 9, wherein the desiccant is positioned less than one inch from the first hydrophilic filter.

14. The water filter system of claim 9, wherein the fluid circuit is translucent allowing visual confirmation of the positioning of the hydrophilic filters and the hydrophobic filter.

* * * * *